United States Patent
Choi et al.

(10) Patent No.: US 10,254,263 B2
(45) Date of Patent: Apr. 9, 2019

(54) AIR CONDITIONING APPARATUS AND METHOD OF DISPLAYING DUST CONCENTRATION USING THE SAME

(71) Applicant: Samsung Electronics Co., Ltd, Gyeonggi-do (KR)

(72) Inventors: Hyeong-hwan Choi, Gyeonggi-do (KR); Yong-keun Jee, Gyeonggi-do (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 289 days.

(21) Appl. No.: 15/177,274

(22) Filed: Jun. 8, 2016

(65) Prior Publication Data

US 2016/0356519 A1    Dec. 8, 2016

(30) Foreign Application Priority Data

Jun. 8, 2015   (KR) ........................ 10-2015-0080504

(51) Int. Cl.

| | |
|---|---|
| *G01V 8/10* | (2006.01) |
| *G01N 33/00* | (2006.01) |
| *F24F 3/16* | (2006.01) |
| *G01V 8/12* | (2006.01) |
| *F24F 11/30* | (2018.01) |
| *F24F 11/77* | (2018.01) |
| *F24F 110/10* | (2018.01) |
| *F24F 110/50* | (2018.01) |
| *F24F 110/64* | (2018.01) |
| *F24F 140/30* | (2018.01) |
| *F24F 11/61* | (2018.01) |
| *F24F 11/52* | (2018.01) |
| *F24F 11/39* | (2018.01) |

(52) U.S. Cl.
CPC ......... *G01N 33/007* (2013.01); *F24F 3/1603* (2013.01); *F24F 11/30* (2018.01); *F24F 11/77* (2018.01); *G01V 8/12* (2013.01); *F24F 11/39* (2018.01); *F24F 11/52* (2018.01); *F24F 11/61* (2018.01); *F24F 2110/10* (2018.01); *F24F 2110/50* (2018.01); *F24F 2110/64* (2018.01); *F24F 2140/30* (2018.01); *Y02A 50/25* (2018.01)

(58) Field of Classification Search
CPC .............. F24F 2110/50; F24F 2110/64; G01N 33/007; G01V 8/12; Y02A 50/25
See application file for complete search history.

(56) References Cited

FOREIGN PATENT DOCUMENTS

WO    WO 02051297 A1 *    7/2002    ........... A47L 9/2815

OTHER PUBLICATIONS

JP 2015-025587 (English Abstract).*

* cited by examiner

*Primary Examiner* — Jonathan Bradford (57) ABSTRACT

A dust concentration display method is provided. The method includes (a) detecting a dust concentration through a dust sensor; (b) displaying a dew condensation message in a display in response to the detected dust concentration being equal to or more than a preset first dust concentration; and (c) detecting the dust concentration in real time for a preset time and displaying the dew condensation message in the display in response to the detected dust concentration being equal to or more than a preset second dust concentration.

13 Claims, 10 Drawing Sheets

DUST CONCENTRATION WILL BE DISPLAYED AS SOON AS DEW CONDENSATION IS REMOVED. PLEASE WAIT A MOMENT. ⎯17

FIG. 5B

CURRENT DUST CONCENTRATION IS 20μg/m³  —17

FIG. 5C

DUST SENSOR IS ERRONEOUS.
PLEASE CONTACT SERVICE CENTER.

FIG. 5D

| FILTER USE PERIOD HAS EXPIRED. PLEASE REPLACE FILTER WITH NEW FILTER. | 17 |

AIR CONDITIONING APPARATUS AND METHOD OF DISPLAYING DUST CONCENTRATION USING THE SAME

CROSS-REFERENCE TO RELATED APPLICATIONS

This application claims priority from Korean Patent Application No. 10-2015-0080504, filed on Jun. 8, 2015, in the Korean Intellectual Property Office, the disclosure of which is incorporated herein by reference in its entirety.

TECHNICAL FIELD

Apparatuses and methods consistent with exemplary embodiments relate to an air conditioning apparatus and a dust concentration display method using the same, and more particularly, to an air conditioning apparatus which determines dew condensation of a dust sensor due to a temperature difference based on a dust concentration detected through the dust sensor provided in the air conditioning apparatus and displays a message corresponding to the determination result and a dust concentration display method using the same.

BACKGROUND

The air conditioning may typically maintain an indoor state suitable for an indoor use purpose by simultaneously adjusting indoor temperature, humidity, ventilation, air, cleaning, and the like. The air conditioning apparatuses may include air conditioners, air cleaners, and the like.

The air cleaners may be an apparatus used to reduce pollutants contained in the indoor air, and a usage amount of the air cleaner has been increasingly increased as concerns on various allergies or diseases due to fine dust are increased in recent years.

The air cleaners may be divided into a filter type, an ionic type, an electrostatic precipitation type, and a water filter type. The filter type may be a mainstream type among the air cleaning types, and the filter type air cleaner may suck air into an air cleaner main body using a fan, purify the polluted air through a filter provided in the inside of the main body, and discharge the purified air to the outside of the main body. The filter type air cleaner may typically employ a method which collects and filters particles in the air using the high efficiency particulate air (HEPA) filter and adsorbs odor using activated charcoal. The products which employ both the filter type and the electrostatic collection type using a plasma effect have been shipped. Other than the activated charcoal, the titanium dioxide photocatalyst may be employed or the ultra low penetration air (ULPA) filter which is a finer filter than the HEPA filter may be employed.

The air cleaners may detect a dust concentration of the air through a dust sensor provided in the inside of the main body and adjust air purification speed by determining a pollution level of the indoor air based on the detected dust concentration.

Figure 1:
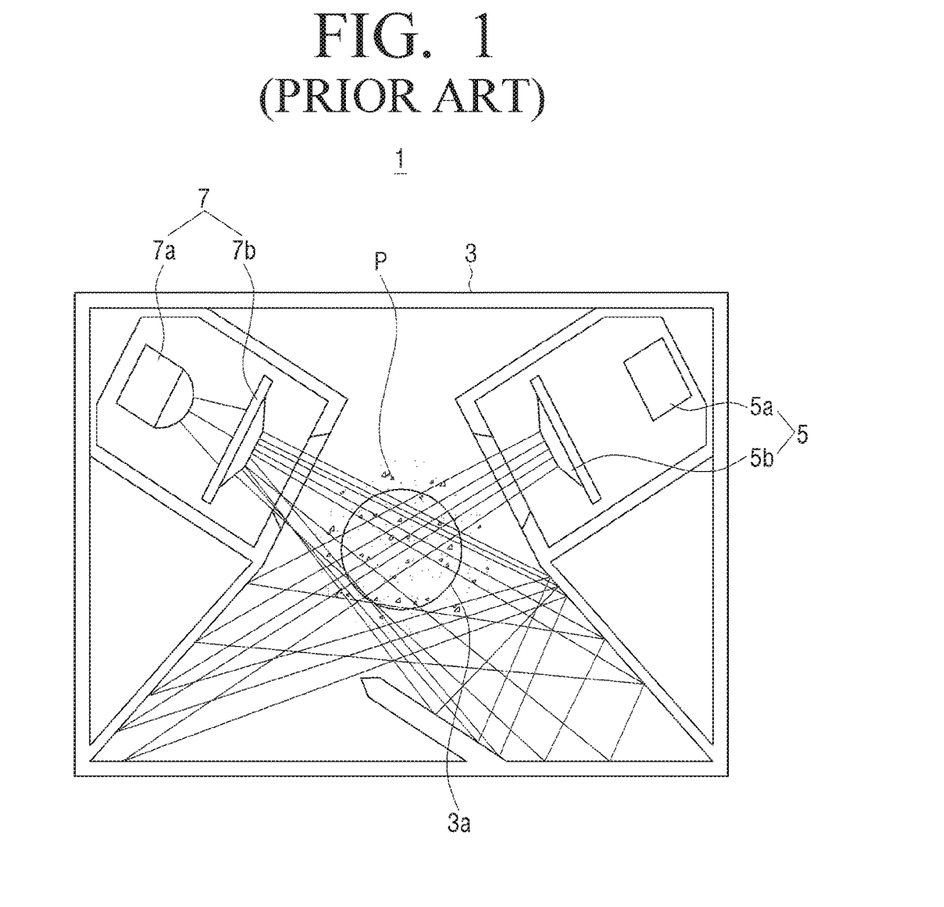
FIG. 1 is a schematic diagram illustrating a structure of a conventional dust sensor.

FIG. 1 illustrates a dust sensor 1 provided in a main body of an air cleaner. The dust sensor 1 may include a light emitter 5 and a light receiver 7 in a housing 3. An air inlet (not shown) and an air outlet 3a which the air flow in and out therethrough may be formed in a front and rear of the housing 3.

The operation of detecting the dust concentration using the dust sensor 1 will be described below. First, light is irradiated toward the air, which flows in the housing 3 through the air inlet, through an infrared light emitting diode (LED) 5a of the light emitter 5. The dust concentration (or the amount of dust) contained in the air may be determined by detecting the amount of light reflected from dust particles P contained in the air through a photo diode of the light receiver 7 and counting a scattered light pulse per unit hour.

In response to the air cleaner which is stored in an outdoor warehouse being installed indoor in the wintertime, dew condensation may occur in surfaces of lenses 5b and 7b provided in the light emitter 5 and the light receiver 7 of the dust sensor 1 due to an abrupt difference between the indoor and outdoor temperatures.

In response to the air cleaner being operated in a state that the dew condensation is formed in the surfaces of the lenses 5b and 7b, the light emitted from the infrared LED 5a of the light emitter 5 is reflected from a plurality of water droplets in the surfaces of the lenses 5b and 7b and thus the amount of light flowing in a light-receiving sensor 7a of the light receiver 7 may be significantly increased.

Accordingly, since it is determined that the dust concentration detected through the dust sensor 1 is high until the water droplets formed in the surfaces of the lenses 5b and 7b are naturally vaporized and removed from the surfaces of the lenses 5b and 7b, the consumers may misunderstand that the use environment (for example, a place in which the air cleaner is installed) is polluted or may determine that the dust sensor is defective, and thus consumer complaints may be increased due to performance degradation of the air cleaner.

SUMMARY

Exemplary embodiments may overcome the above disadvantages and other disadvantages not described above. Also, an exemplary embodiment is not required to overcome the disadvantages described above, and an exemplary embodiment may not overcome any of the problems described above.

One or more exemplary embodiments relate to a dust concentration display method capable of increasing product reliability and consumer satisfaction degree by detecting a dust concentration in consideration of a time that dew condensation formed in a lens of a dust sensor is disappeared and preventing misrecognition of the user that the product is defective due to the dew condensation.

According to an aspect of an exemplary embodiment, there is provided a method of displaying a dust concentration, the method including (a) detecting a dust concentration through a dust sensor; (b) displaying a dew condensation message in a display in response to the detected dust concentration being equal to or more than a preset first dust concentration; and (c) detecting the dust concentration in real time for a preset time and displaying the dew condensation message in the display in response to the detected dust concentration being equal to or more than a preset second dust concentration.

The method may further include, after operation (c), (d) displaying an error message in the display in response to the dust concentration detected after the preset time elapsed being equal to or more than the preset first dust concentration.

The second dust concentration may have a smaller dust concentration value than the first dust concentration.

The dust concentration may be displayed in the display in response to the detected dust concentration being less than the preset first dust concentration in operation (b).

The dust concentration may be displayed in the display in response to the detected dust concentration being less than the preset second dust concentration in operation (c).

The method may further include calculating a total operation time of an air conditioning apparatus and displaying a filter change message in response to the total operation time being larger than a preset filter change time.

The method may further include initializing the operation time of the air conditioning apparatus in response to a filter mounted on the air conditioning apparatus being replaced.

The dew condensation message may indicate that the normal dust concentration detection operation is not performed in the dust sensor due to the dew condensation which is formed in a surface of a lens provided in the dust sensor in response to the air conditioning apparatus being moved from a first position to a second position in which a temperature is higher than that of the first position. An error message for the dust sensor may be displayed in response to the dust concentration being equal to or more than the first dust concentration and the temperature in the second position being room temperature in operation (d).

According to an aspect of an exemplary embodiment, there is provided a method of displaying a dust concentration, the method including operating an air conditioning apparatus; counting an operation time of the air conditioning apparatus; displaying a dew condensation message in response to a dust concentration detected through a dust sensor being equal to or more than a preset first dust concentration and displaying the dust concentration in response to the dust concentration being less than the first dust concentration; detecting the dust concentration in real time for a preset time, displaying the dew condensation message in response to the detected dust concentration being equal to or more than a second dust concentration which is smaller than the first dust condensation, and displaying the dust concentration in response to the detected dust concentration being less than the second dust concentration; and displaying an error message for the dust sensor in response to the dust concentration detected after the preset time elapsed being equal to or more than the first dust concentration.

According to an aspect of an exemplary embodiment, there is provided an air conditioning apparatus which processes air sucked into an inside of a main body and discharges the processed air to an outside of the main body, the air conditioning apparatus including a dust sensor disposed in the inside of the main body and configured to detect a dust concentration of air flowing in the inside of the main body; a display configured to display a message based on the dust concentration detected through the dust sensor; and a controller configured to control the display to display a dew condensation message in response to the dust concentration, which is firstly detected through the dust sensor after the air conditioning apparatus is operated, being equal to or more than a preset first dust concentration and to display the dew condensation message in response to the dust concentration, which is detected in real time for a preset time through the dust sensor, being equal to or more than a preset second dust concentration.

Additional aspects and advantages of the exemplary embodiments are set forth in the detailed description, and will be obvious from the detailed description, or may be learned by practicing the exemplary embodiments.

BRIEF DESCRIPTION OF THE DRAWINGS

The above and/or other aspects of the present invention will be more apparent by describing certain exemplary embodiments of the present invention with reference to the accompanying drawings, in which.

DETAILED DESCRIPTION

Hereinafter, the exemplary embodiments are described in greater detail with reference to the accompanying drawings.

In the following description, unless otherwise described, the same reference numerals are used for the same elements when they are depicted in different drawings. The matters defined in the description, such as detailed construction and elements, are provided to assist in a comprehensive understanding of the exemplary embodiments. Thus, it is understood that the exemplary embodiments can be carried out without those specifically defined matters. Also, functions or elements known in the related art are not described in detail since they would obscure the exemplary embodiments with unnecessary detail.

An air conditioning apparatus 10 in the exemplary embodiment may be various industrial and household air conditioning apparatuses which perform air conditioning such as an air cleaner, an air conditioner, and a hot air blower.

Figure 2:
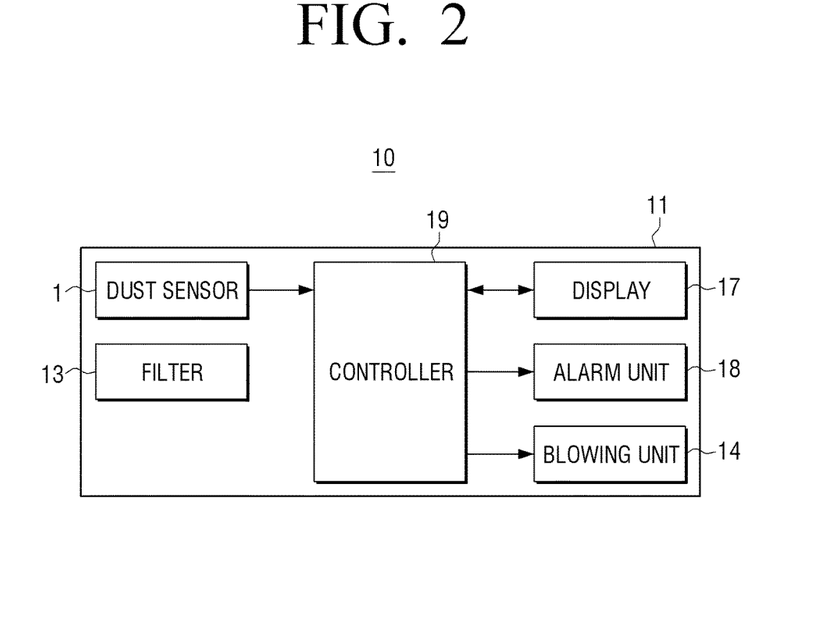
FIG. 2 is a block diagram illustrating an air conditioning apparatus which performs a dust concentration display method according to an exemplary embodiment.

Referring to FIG. 2, the air conditioning apparatus 10 may have substantially the same configuration as a conventional air conditioning apparatus. That is, the air conditioning apparatus 10 may include a dust sensor (see 1 of FIG. 1), a case 11, a filter 13, a blowing unit 14, a display 17, an alarm unit 18, and a controller 19.

The dust sensor 1 may have substantially the same configuration as the dust sensor 1 illustrated in FIG. 1. The dust senor 1 may be electrically coupled to the controller 19 and transmit a detection signal with respect to the detected dust concentration (or dust amount) to the controller 19. An air outlet 3a of the dust sensor 1 may be coupled to a certain duct of the blowing unit 14 and may suck the air into a housing 3 using suction force generated in the blowing unit 14.

The case 11 may include an air inlet (not shown) configured to suck the air into the inside thereof, a filter configured to filter the sucked air, and an air outlet configured to discharge the air filtered through the filter 13.

The blowing unit 14 configured to generate the suction force to suck the air in the outside of the case 11 into the inside of the case 11 through the air inlet, the dust sensor 1, the display 17, the alarm unit 18, and the controller 19 may be built in the case 11.

The blowing unit 14 may be communicated with the air inlet and the air outlet through a certain duct (not shown), and an amount of air to be purified may be adjusted by controlling speed of a fan (not shown) of the blowing unit 14 through the controller 19.

The display 17 may be electrically coupled to the controller 19 and display status information of the air conditioning apparatus 10 (for example, power on/off of the air conditioning apparatus 10, blowing/non-blowing, blowing level, dust amount, normal operation/abnormal operation of the sensor, and the like) provided from the controller 19. The display unit 17 may be disposed to be exposed toward the outside of the case 11, and may be configured of a touch screen which may receive a user command.

The alarm unit 18 may be configured of a speaker unit to notify the user of the status information of the air conditioning apparatus 10 in an auditory form. The alarm unit 18 may be electrically coupled to the controller 19 and may be operated through the controller 19.

Although not shown in FIG. 2, various buttons which input user commands may be disposed in the case 11 of the air conditioning apparatus 10.

Figure 3:
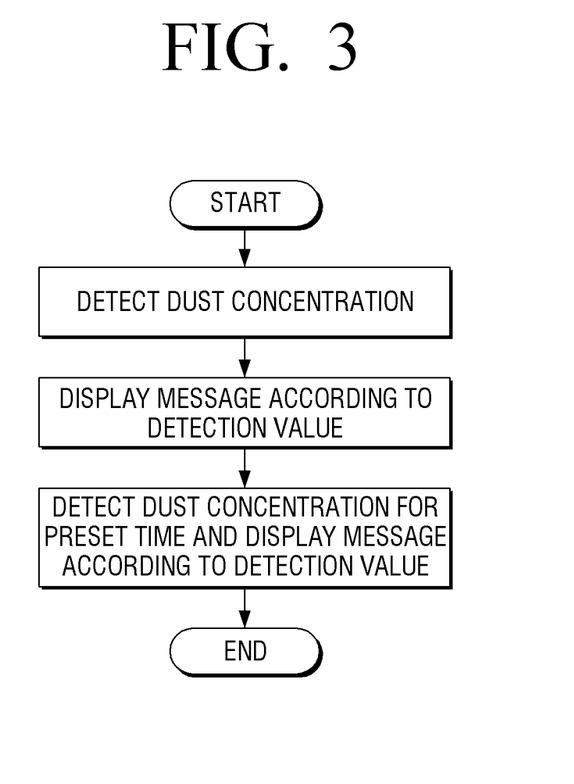
FIG. 3 is a schematic flowchart illustrating a dust concentration display process according to an exemplary embodiment.

Hereinafter, a dust concentration display method performed in the air conditioning apparatus 10 having the above-described configuration according to an exemplary embodiment will be described with reference to FIGS. 3 and 4.

First, the dust concentration display method will be schematically described with reference to FIG. 3. To perform the dust concentration display method, the air conditioning apparatus 10 may display a dew condensation message or a dust concentration in the display 17 based on a dust concentration which is firstly detected through the dust sensor 1 after the air conditioning apparatus 10 which is moved from the outside to the inside and installed in the inside is operated.

The air conditioning apparatus 10 may detect the dust concentration in real time for a preset time through the dust sensor 1 and display the dew condensation message or the dust concentration in the display 17 based on the detected dust concentration again.

The air conditioning apparatus 10 may provide the user the information that the dust sensor 1 is abnormally operated due to the dew condensation caused by the difference between the indoor and outdoor temperatures in response to the air conditioning apparatus 10 being installed in the inside in wintertime, and may notify the user of the information that the air conditioning apparatus 10 is not abnormal.

The controller 19 may control the blowing unit 14 to be driven in a normal mode while the dust sensor 1 is abnormally operated due to the dew condensation.

Hereinafter, the dust concentration display method according to an exemplary embodiment will be described in detail with reference to FIG. 4.

In response to the air conditioning apparatus 10 which is stored in a warehouse of a factory and the like being moved to the inside of a building of a consumer and installed in the inside in the wintertime, since the temperature in the building may be higher than the temperature in the warehouse, a plurality of water droplets may be formed in the surfaces of the lens 5b and 7b of the dust sensor 1 provided in the air conditioning apparatus 10 due to the dew condensation by the temperature difference.

In the exemplary embodiment, the controller 19 may control the air conditioning apparatus 10 to perform a normal operation by preventing the user from determining that the dust sensor malfunctions due to the dew condensation through the following process.

First, the controller 19 may turn on the air conditioning apparatus 10 by supplying external power to the air conditioning apparatus 10 installed inside, and then operate the air conditioning apparatus 10 based on an air cleaning command of the user. The power of the air conditioning apparatus 10 is turned on and simultaneously the air conditioning apparatus 10 may perform the air cleaning operation.

The controller 19 may count an operation time of the air conditioning apparatus 10 (S1). The counting of the operation time of the air conditioning apparatus 10 is to determine a change time of the filter 13 provided in the air conditioning apparatus 10.

After the counting of the operation time of the air conditioning apparatus 10 starts, the controller 19 may determine whether or not the dust concentration detected through the dust sensor 1 is equal to or more than a first dust concentration (S2).

The first dust concentration may be set to a value corresponding to a dust concentration detectable in response to an amount of light, which is emitted from the infrared LED 5a of the light emitter 5, reflected from the plurality of water droplets formed in the surfaces of the lenses 5b and 7b, and flows in the light-receiving sensor 7a of the light receiver 7 in the operation of the air conditioning apparatus 10 in a state that the dew condensation is formed in the surfaces of the lenses 5b and 7b, being considerably increased. The first dust concentration may be set to 999 $\mu g/m^3$ close to the maximum value of the dust concentration which is detectable through the dust sensor 1. However, the value of the first dust concentration is merely exemplary and is not an absolute value. The first dust concentration value may be changed according to the using environment or purpose of the air conditioning apparatus 10.

In response to the dust concentration detected through the dust sensor 1 being equal to or more than the first dust concentration, the controller 19 may determine that the normal operation of the dust sensor 1 is not yet performed due to the dew concentration occurring in the dust sensor 1, and control the display 17 to display the dew condensation message indicating that the dew condensation occurs in the dust sensor 1 (S3). For example, the message that "Dust concentration will be displayed as soon as the dew condensation is removed. Please wait a moment." may be displayed in the display 17 as illustrated in FIG. 5A and thus the controller 19 may notify the user of the information that the dust sensor 1 is not defective.

In response to the dust concentration detected through the dust sensor 1 being less than the first dust concentration, the controller 19 may determine that the dust sensor 1 is normally operated, and control the display 17 to display the detected dust concentration with a specific number (S8). For example, the message that "Current dust concentration is 20 $\mu g/m^3$." may be displayed in the display 17 as illustrated in FIG. 5B.

For example, in response to the dew condensation message being displayed, the controller 19 may determine whether or not the dust concentration detected in real time for a preset time through the dust sensor 1 is equal to or more than a second dust concentration.

In this example, the controller 19 may determine whether or not the preset time elapsed (S4). The preset time may be a time sufficient to remove the dew condensation formed in the surfaces of the lenses 5b and 7b of the dust sensor 1 through nature vaporization (for example, about two hours).

The preset time may be changed according to the temperature of a place in which the air conditioning apparatus 10 is used.

In response to the preset time being not elapsing, the controller 19 may determine whether or not the dust concentration being equal to or more than the second dust concentration (S5). In response to the dust concentration being equal to or more than the second dust concentration, the controller 19 may control the display 17 to display the dew condensation message (S3) and in response to the dust concentration being less than the second dust concentration, the controller 19 may control the display 17 to display the dust concentration (S8). The second dust concentration may be about 899 μg/m$^3$ by 100 μg/m$^3$ smaller than the first dust concentration (999 μg/m$^3$). However, like the value of the first dust concentration, the value of the second dust concentration is merely exemplary and is not an absolute value. The second dust concentration value may be changed according to the using environment or purpose of the air conditioning apparatus 10.

In response to the preset time being elapsing, the controller 19 may determine whether or not the dust concentration is equal to or more than the first dust concentration (S6). In response to the dust concentration being equal to or more than the firs setup concentration, the controller 19 may determine that an error is generated in the dust sensor 1 itself, and the controller 19 may control the display 17 to display an error message (S7). For example, the message that "Dust sensor is erroneous. Please contact service center." may be displayed in the display 17 as illustrated in FIG. 5C, and the controller 19 may notify the user of the information that the dust sensor 1 is defective.

In response to the dust concentration being less than the first dust concentration, the controller 19 may control the display 17 to display the dust concentration with a specific number (S8).

In operation S6, the first dust concentration is used as the criterion for determining the display of the error message, but this is not limited thereto, and the second dust concentration may be used as the criterion for determining the display of the error message. This is because the appropriate criterion is used in consideration of performance (for example, detection range of the dust concentration and the like) of the dust sensor 1 employed in the air conditioning apparatus 10.

In response to the dust concentration being displayed through the display 17, the controller 19 may determine that the dew condensation formed in the lenses 5b and 7b of the dust sensor 1 is disappeared and the dust sensor 1 is normally operated.

The controller 19 may calculate a total operation time in real time and determine whether or not the calculation value is larger than a preset filter change time (S9). In response to the total operation time being larger than the filter change time, the controller 19 may control the display 17 to display a filter change message or may control the alarm unit 18 to output a sound for notifying filter change (S10). In operation S10, the message that "Filter use period has expired. Please replace filter with new filter." may be displayed in the display 17 as illustrated in FIG. 5D and the controller 19 may induce the user to replace the filter through the message. The alarm unit 18 may output the sound corresponding to the message displayed in the display 17.

In response to the new filter being replaced in the air conditioning apparatus 10, the controller 19 may initialize the operation time (set the operation time to zero (0)) so as to count the filter change time of the new filter (S11).

In the exemplary embodiment, through the dust concentration detection process, the misunderstanding of the user that the product is defective due to dew condensation formed in the dust sensor 1 may be prevented, and thus the product reliability may be maintained and the satisfaction degree of the user may be increased.

Figure 6:
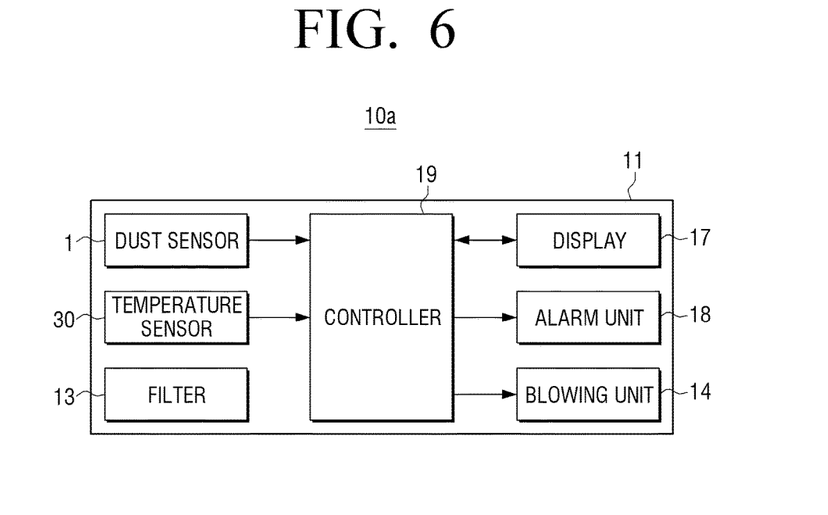
FIG. 6 is a block diagram illustrating an air conditioning apparatus which implements a dust concentration display method according to another exemplary embodiment.

The dust concentration display method according to an exemplary embodiment may be implemented through an air conditioning apparatus 10a illustrated in FIG. 6.

The air conditioning apparatus 10a illustrated in FIG. 6 may have substantially the same configuration as the air conditioning apparatus 10 illustrated in FIG. 2, but the air conditioning apparatus 10a is different from the air conditioning apparatus 10 in that a temperature sensor 30 is included.

Figure 4:
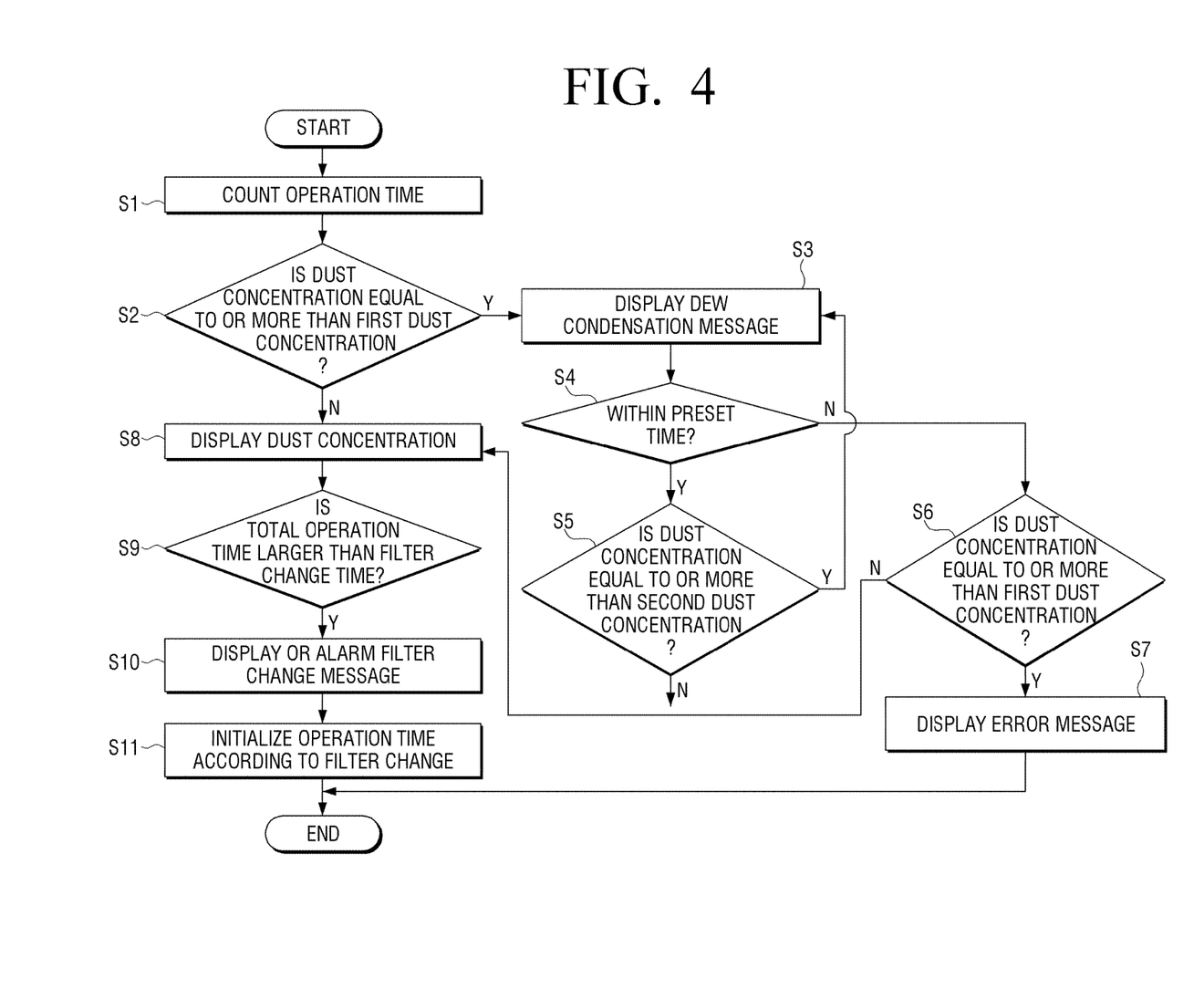
FIG. 4 is a detailed flowchart illustrating a dust concentration display process of FIG. 3 according to an exemplary embodiment.
Figure 5A:
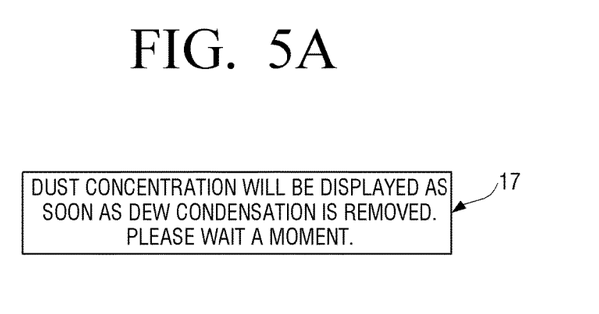
FIGS. 5A to 5D are diagrams illustrating messages displayed in a display in operations illustrated in FIG. 4.
Figure 5B:
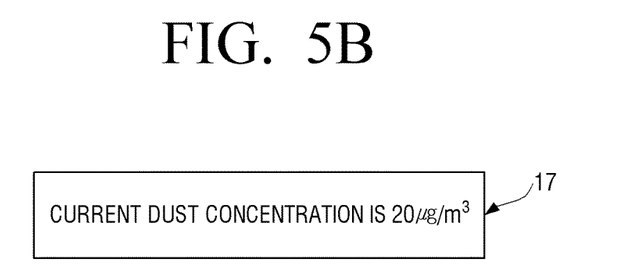
Figure 5C:
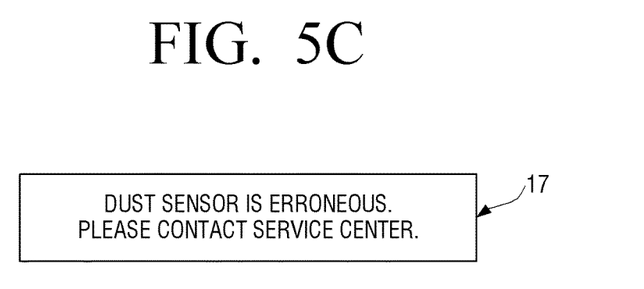
Figure 5D:
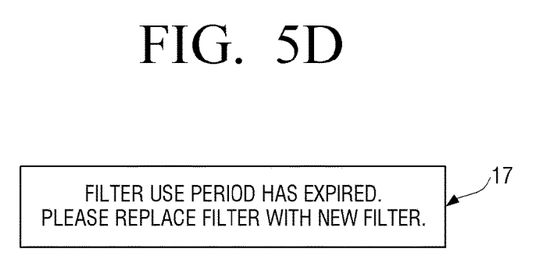

A dust concentration display method implemented through the air conditioning apparatus 10a further including the temperature sensor 30 may be substantially the same as the dust concentration display method implemented through the air conditioning apparatus 10 illustrated in FIG. 4, but the dust concentration display method is different from the method in FIG. 4 in that a process of determining whether or not a temperature of a place in which the air conditioning apparatus 10a is installed is room temperature is further performed.

Figure 7:
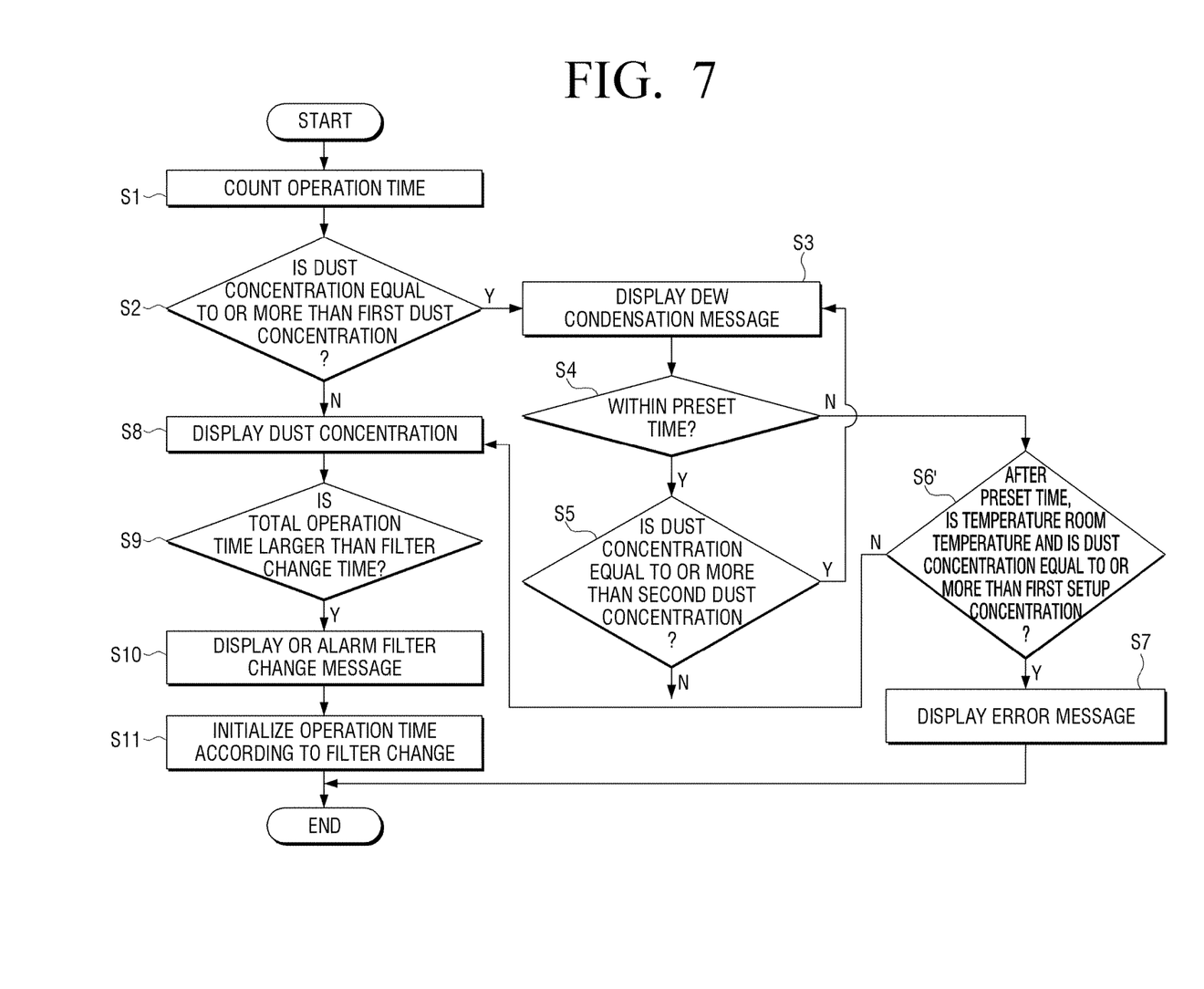
FIG. 7 is a detailed flowchart illustrating a dust concentration display process in an air conditioning apparatus according to another exemplary embodiment.

Referring to FIG. 7, in response to the preset time being elapsed as the determination result in operation S4, the controller 19 may determine whether or not the dust concentration is equal to or more than the first dust concentration and whether or not a current temperature detected through the temperature sensor 30 is room temperature (S6'). In response to the two conditions being satisfied, the controller 19 may control the display 17 to display an error message.

Since the operation for determining whether or not the temperature of the place in which the air conditioning apparatus 10a installed is the room temperature is performed after the preset time elapsed, the controller 19 may determine that the water droplets formed in the surfaces of the lends 5b and 7b of the dust sensor 1 are previously naturally vaporized. Accordingly, in response to the two condition that the dust concentration detected through the dust sensor 1 is equal to or more than the first dust concentration and the temperature is the room temperature being satisfied, the controller 19 may determine that an error of the dust sensor 1 itself may occur other than the abnormal operation of the dust sensor 1 due to the dew condensation.

The dust concentration display method may include the process of determining whether or not the temperature is the room temperature through the temperature 30, and thus the accuracy with respect to the error (failure) determination of the dust sensor 1 itself may be improved.

The dust sensor in the exemplary embodiment is a dust sensor using a method of detecting an amount of light according to reflection from the dust, but this is not limited thereto. A conventional light-blocking type dust sensor which determines the dust concentration by detecting an amount of light blocked through the dust may be employed. Even in response to the light-blocking type dust sensor being employed, the problem that the amount of light is increased due to the dew condensation formed in the lens may be caused, and the problem caused due to the dew condensation may be overcome through the dust concentration display method in the exemplary embodiment.

The foregoing exemplary embodiments and advantages are merely exemplary and are not to be construed as limiting the present invention. The present teaching can be readily applied to other types of apparatuses. Also, the description of the exemplary embodiments of the present invention is intended to be illustrative, and not to limit the scope of the claims, and many alternatives, modifications, and variations will be apparent to those skilled in the art.

What is claimed is:

1. A method of displaying a dust concentration, the method comprising:
   (a) detecting a dust concentration through a dust sensor;
   (b) displaying a dew condensation message in a display in response to the detected dust concentration being equal to or more than a preset first dust concentration; and
   (c) detecting the dust concentration for a preset time and displaying the dew condensation message in the display in response to the detected dust concentration being equal to or more than a preset second dust concentration.

2. The method as claimed in claim 1, further comprising, after operation (c), (d) displaying an error message in the display in response to the dust concentration detected after the preset time elapsed being equal to or more than the preset first dust concentration.

3. The method as claimed in claim 1, wherein the preset second dust concentration has a smaller dust concentration value than the preset first dust concentration.

4. The method as claimed in claim 1, wherein the dust concentration is displayed in the display in response to the detected dust concentration being less than the preset first dust concentration in operation (b).

5. The method as claimed in claim 1, wherein the dust concentration is displayed in the display in response to the detected dust concentration being less than the preset second dust concentration in operation (c).

6. The method as claimed in claim 1, further comprising calculating a total operation time of an air conditioning apparatus and displaying a filter change message in response to the total operation time being larger than a filter change time.

7. The method as claimed in claim 6, further comprising initializing the total operation time of the air conditioning apparatus in response to a filter mounted on the air conditioning apparatus being replaced.

8. The method as claimed in claim 2, wherein the dew condensation message indicates that the normal dust concentration detection operation is not performed in the dust sensor due to the dew condensation which is formed in a surface of a lens provided in the dust sensor in response to an air conditioning apparatus being moved from a first position to a second position in which a temperature is higher than that of the first position.

9. The method as claimed in claim 8, wherein an error message for the dust sensor is displayed in response to the dust concentration being equal to or more than the preset first dust concentration and the temperature in the second position being room temperature in operation (d).

10. A method of displaying a dust concentration, the method comprising:
    operating an air conditioning apparatus;
    counting an operation time of the air conditioning apparatus;
    displaying a dew condensation message in response to a dust concentration detected through a dust sensor being equal to or more than a preset first dust concentration and displaying the dust concentration in response to the dust concentration being less than the preset first dust concentration;
    detecting the dust concentration for a preset time when the dust concentration is equal to or more than the preset first dust concentration;
    during the preset time, displaying the dew condensation message in response to the detected dust concentration being equal to or more than a second dust concentration which is smaller than the preset first dust concentration, and displaying the dust concentration in response to the detected dust concentration being less than the second dust concentration; and
    displaying an error message for the dust sensor in response to the dust concentration detected after the preset time elapsed being equal to or more than the preset first dust concentration.

11. An air conditioning apparatus which processes air sucked into an inside of a main body and discharges the processed air to an outside of the main body, the air conditioning apparatus comprising:
    a dust sensor disposed in the inside of the main body and configured to detect a dust concentration of air flowing in the inside of the main body;
    a display configured to display a message according to the dust concentration detected through the dust sensor; and
    a controller configured to control the display to display a dew condensation message in response to the dust concentration, which is firstly detected through the dust sensor after the air conditioning apparatus is operated, being equal to or more than a preset first dust concentration and to display the dew condensation message in response to the dust concentration, which is detected for a preset time through the dust sensor, being equal to or more than a preset second dust concentration.

12. The air conditioning apparatus as claimed in claim 11, wherein the controller controls the display to display an error message in response to the dust concentration, which is detected after the preset time elapsed, being the preset first dust concentration.

13. The air conditioning apparatus as claimed in claim 12, further comprising a temperature sensor configured to detect a temperature of a place in which the air conditioning apparatus is installed,
    wherein the controller determines whether or not the temperature of the place is room temperature before the dew condensation message is displayed in response to the dust concentration detected for the preset time being equal to or more than the preset first dust concentration and controls the display to display the error message for the dust sensor in response to the temperature of the place being the room temperature.

* * * * *